United States Patent
Sayegh

(10) Patent No.: US 12,251,304 B2
(45) Date of Patent: Mar. 18, 2025

(54) SELECTION OF TORIC INTRAOCULAR LENSES

(71) Applicant: Samir Sayegh, Champaign, IL (US)

(72) Inventor: Samir Sayegh, Champaign, IL (US)

( * ) Notice: Subject to any disclaimer, the term of this patent is extended or adjusted under 35 U.S.C. 154(b) by 854 days.

(21) Appl. No.: 17/472,651

(22) Filed: Sep. 12, 2021

(65) Prior Publication Data

US 2022/0079746 A1    Mar. 17, 2022

Related U.S. Application Data

(60) Provisional application No. 63/077,687, filed on Sep. 13, 2020.

(51) Int. Cl.
  *A61F 2/16*   (2006.01)
  *G16H 40/20*  (2018.01)
  *G16H 50/30*  (2018.01)

(52) U.S. Cl.
  CPC ........... *A61F 2/1645* (2015.04); *G16H 40/20* (2018.01); *G16H 50/30* (2018.01); *A61F 2240/002* (2013.01)

(58) Field of Classification Search
  CPC . A61F 2/1645; A61F 2240/002; G16H 40/20; G16H 50/30; G16H 20/30; G16H 50/20; A61B 3/0025
  USPC ......................................................... 351/241
  See application file for complete search history.

(56) References Cited

U.S. PATENT DOCUMENTS

| | | | |
|---|---|---|---|
| 9,456,894 B2* | 10/2016 | Zhao | G02C 7/04 |
| 10,398,544 B2* | 9/2019 | Sayegh | A61F 2/1645 |
| 2009/0323020 A1* | 12/2009 | Zhao | G02C 7/045 |
| | | | 623/6.29 |
| 2010/0152847 A1* | 6/2010 | Padrick | A61B 3/13 |
| | | | 623/6.11 |
| 2015/0062529 A1 | 3/2015 | Kasthurirangan et al. | |
| 2016/0302915 A1 | 10/2016 | Sayegh | |

FOREIGN PATENT DOCUMENTS

| | | |
|---|---|---|
| JP | 2014131742 | 7/2014 |
| WO | 2010/096492 | 8/2010 |
| WO | 2012/120080 | 9/2012 |
| WO | WO 2013/159076 A2 | 10/2013 |

OTHER PUBLICATIONS

Beheregaray et al., "Astigmatic overcorrection and axis flip for targeting minimal remaining refractive astigmatism with toric intraocular lenses," J Cataract Refract Surg. 44(1), 2018, pp. 91-97.

Gabra et al., "A Direct Method for Determining Toricity Ratios of Toric Intraocular Lens Calculators," Sci Rep. doi:10.1038/s41598-018-22591-4, Mar. 15, 2018, pp. 1-8.

(Continued)

*Primary Examiner* — Mohammed A Hasan
(74) *Attorney, Agent, or Firm* — Mueting Raasch Group

(57) ABSTRACT

Various embodiments of selection of a toric intraocular lens (tIOL) for use in correcting an astigmatism using are disclosed. One of an overcorrecting tIOL and an undercorrecting tIOL may be selected based on, among other things, an estimated misalignment. The estimated misalignment may include all contributions to misalignment of a tIOL when implanted.

23 Claims, 11 Drawing Sheets

(56) References Cited

OTHER PUBLICATIONS

Savini et al., "Influence of axial length and corneal power on the astigmatic power of toric intraocular lenses," J Cataract Refract Surg, doi:10.1016/j.jcrs.2013.04.047, 2013, 4 pages.
Sayegh et al., Three Shades of Grey: Toric IOL Choices and Principled Uncertainty. In: Meeting of The American Society of Cataract and Refractive Surgeons (ASCRS) 2019. San Diego, CA, 2019.
Sayegh, "Consequences of Mismatch, Misalignment and Rotation of Toric Intraocular Lenses in Refractive Cataract Surgery. Part 1. It Ain't 30. The True Angle of Doom," doi:10.1101/2020.06.09.20126987, Jun. 2020, 15 pages.
Sayegh, "Consequences of Mismatch, Misalignment, and Rotation of Toric Intraocular Lenses in Refractive Cataract Surgery Part 2. Avoiding Flip Flops", medRxiv, doi: https://doi.org/10.1101/2020.09.30.20203380, Sep. 30, 2020, 26 pages.
International Search Report and Written Opinion from PCT Application No. PCT/US2021/049979 dated Dec. 24, 2021, 13 pages.
European Patent Application No. 21867727.6, filed Mar. 27, 2023; Extended European Search Report issued Sep. 24, 2024.

\* cited by examiner

| Calculation Method | |
|---|---|
| ○ Abulafia-Koch Regression ● Standard K | |

Pre-Surgery Details

| IOL model | Ankoris (Pod T) |
|---|---|
| Eye selection | ●OD  ○OS |

Keratometry

K Notation ●Diopter (D) ○Millimeter (mm)

| Flat K | 42.72 D | @ Axis | 180 ° |
|---|---|---|---|
| Steep K | 46.00 D | @ Axis | 90 ° |
| SIA | 0.00 D | Axis of Incision | 0 ° |

Biometry

| Axial Length | 24.00 mm | ACD | 3.00 mm |
|---|---|---|---|
| A-Constant | 118.95 | | |

Calculation Preferences

| Calc. SE power of IOL | 20.0 D | K index | 1.3375 |
|---|---|---|---|

Calculate

Results

Anticipated residual astigmatism

| Select | IOL | Power | Axis |
|---|---|---|---|
| ○ | Lens #1 +20.00D CYL 4.50D | 0.26 D | 90 |
| ●✓ | Lens #2 +20.00D CYL 5.25D | 0.25 D | 180 |
| ○ | Lens #3 +20.00D CYL 6.00D | 0.76 D | 180 |

FIG. 5

| Calculation Method | |
|---|---|
| ● Abulafia-Koch Regression ○ Standard K | |

| Pre-Surgery Details | |
|---|---|
| IOL model | Ankoris (Pod T) |
| Eye selection | ●OD ○OS |

| Keratometry | | | |
|---|---|---|---|
| K Notation ● Diopter (D) ○ Millimeter (mm) | | | |
| Flat K | 42.46 D | @ Axis | 180 ° |
| Steep K | 46.00 D | @ Axis | 90 ° |
| SIA | 0.00 D | Axis of Incision | 0 ° |

| Biometry | | | |
|---|---|---|---|
| Axial Length | 24.00 mm | ACD | 3.00 mm |
| A-Constant | 118.95 | | |

| Calculation Preferences | | | |
|---|---|---|---|
| Calc. SE power of IOL | 20.0 D | K index | 1.3375 |
| Calculate | | | |

| Results | | | |
|---|---|---|---|
| | Anticipated residual astigmatism | | |
| Select | IOL | Power | Axis |
| ○ | Lens #1 +20.00D CYL 3.75D | 0.26 D | 90 |
| ●✓ | Lens #2 +20.00D CYL 4.50D | 0.25 D | 180 |
| ○ | Lens #3 +20.00D CYL 5.25D | 0.76 D | 180 |

Keratometry

SIA: 0.00 D @Meridian (incision location): 180°

Flat K1: 42.67 D Flat K1 @ Meridian: 180°

Steep K2: 46.00 D Steep K2 @ Meridian: 90°

Preop Corneal Astigmatism: 3.33 D ☑ include posterior corneal astigmatism

Biometry

Axial Length: 24.00 mm
Method: Optical or Immersion
A-constant: 119.30

Calculation Preferences

SE IOL Power: 20.0 D
K Index: 1.3375
Refractive Cylinder Convention: ●Plus ○Minus

Final Results

| IOL Details | | | Residual Astigmatism | |
|---|---|---|---|---|
| IOL Model | Orientation | | Cylinder | Axis |
| ZCU375 | 90° | | 0.26D | 90° |
| ZCU450 | 90° | | 0.24D | 0° |
| ZCU525 | 90° | | 0.73D | 0° |

FIG. 8

| IOL Refractive Power | | | | Predicted Outcome | | | | |
|---|---|---|---|---|---|---|---|---|
| SE [D] | Sph [D] | Cyl [D] | Axis [°] | SE [D] | Sph [D] | Cyl [D] | Axis [°] | ELP |
| + | | + | | | | | | + |
| +16.50 | +11.50 | +10.00 | 90 | -0.24 | -0.30 | +0.13 | 0 | 4.39 |
| - | | - | | | | | | - |

FIG. 9

SELECTION OF TORIC INTRAOCULAR LENSES

This application claims the benefit of U.S. Provisional Patent Application No. 63/077,687, filed Sep. 13, 2020, the disclosure of which is incorporated by reference herein in its entirety.

This disclosure generally relates to treatment of astigmatism with toric intraocular lenses, and in particular to the selection of toric intraocular lenses.

Astigmatism results from refractive errors caused by an asymmetric or irregularly shaped cornea or changes in the curvature of the lens inside the eye affecting the bending or refraction of light in the eye. Astigmatism usually causes blurred or distorted vision at all distances and where uncorrected, can lead to eyestrain, headaches, and fatigue with prolonged visual tasks.

Astigmatism can be corrected during cataract surgery by replacing the natural lens with a correcting toric intraocular lens (tIOL). However, tIOLs usually provide only discrete astigmatism correcting power, and furthermore, selecting a suitable tIOL can be an error-prone process, resulting in overcorrection or undercorrection, yielding suboptimal results and potentially necessitating permanent dependence on eyeglasses or further surgical procedures.

Toric calculators, used to select a suitable tIOL, attempt to prevent these and other problems but are often limited in their understanding and implementation of the optical principles underlying image formation and perception. More recently, some toric calculators have migrated to a "split-the-difference" strategy where overcorrection is always accepted/selected if the residual provided by the overcorrecting tIOL is less than that of the undercorrecting one. However, the decision of overcorrecting may be more subtle than originally considered and further adaptions and considerations can be made to improve accuracy and suitability of overcorrection versus undercorrection decisions.

SUMMARY

This disclosure generally relates to various embodiments of selection of tIOLs based on, among other things, estimated misalignment of the tIOL and lens information for two or more tIOLS.

In one embodiment, a method for selecting a tonic intraocular lens (tIOL) can comprise: receiving lens information for an overcorrecting tIOL and an undercorrecting tIOL for an eye to be treated with the selected tIOL; receiving an estimated misalignment; and selecting one of the overcorrecting tIOL and the undercorrecting tIOL based on the lens information for the overcorrecting tIOL and the undercorrecting tIOL, and the estimated misalignment. The selecting can further comprise determining a minimum astigmatism; and selecting one of the overcorrecting tIOL and the undercorrecting tIOL based on the minimum astigmatism and astigmatism to be corrected. The selecting can further comprise generating astigmatism to be corrected based on measured eye information. The selecting can further comprise generating astigmatism to be corrected based on the lens information. The minimum astigmatism can be determined based on at least the estimated misalignment and on the lens information. Selecting one of the overcorrecting tIOL and the undercorrecting tIOL can comprise selecting the overcorrecting tIOL if the minimum astigmatism is less than the astigmatism to be corrected. The selecting can further comprise determining a maximum astigmatism; and selecting one of the overconecting tIOL and the undercorrecting tIOL based on the maximum astigmatism and astigmatism to be corrected. The maximum astigmatism can be based on at least the estimated misalignment and the lens information. The lens information can include an overcorrection value that indicates an amount of overcorrecting that would occur with the overcorrecting tIOL. Selecting one of the overcorrecting tIOL and the undercorrecting tIOL can comprise selecting the overcorrecting tIOL if the overcorrection value is less than a maximum astigmatism to be overcorrected. The method can further comprise receiving user input comprising at least one of estimated misalignment, eye information, and lens information. The method can further comprise receiving user input comprising at least one of estimated misalignment, eye information, and lens information. The method can further comprise displaying, on a user display, selected tIOL information.

A system for selecting a tIOL can comprise processing circuitry configured to receive lens information for an overcorrecting tIOL and an undercorrecting tIOL for an eye to be treated with the selected tIOL; receive an estimated misalignment; and select one of the overcorrecting tIOL and the undercorrecting tIOL based on the lens information for the overcorrecting tIOL and the undercorrecting tIOL, and the estimated misalignment. The processing circuitry can be further configured to determine a minimum astigmatism; and select one of the overcorrecting tIOL and the undercorrecting tIOL based on the minimum astigmatism and astigmatism to be corrected. The selecting can further comprise generating astigmatism to be corrected based on measured eye information. The selecting can further comprise generating astigmatism to be corrected based on the lens information. The minimum astigmatism can be determined based on at least the estimated misalignment and on the lens information. The processing circuitry can be further configured to determine a maximum astigmatism; and select one of the overcorrecting tIOL and the undercorrecting tIOL based on the maximum astigmatism and astigmatism to be corrected. The maximum astigmatism can be based on at least the estimated misalignment and the lens information. The lens information includes an overcorrection value that indicates an amount of overcorrecting that would occur with the overcorrecting tIOL. The processing circuitry can be further configured to select one of the overcorrecting tIOL and the undercorrecting by selecting the overcorrecting tIOL if the overcorrection value is less than a maximum astigmatism to be overcorrected. The system can further comprise input apparatus to allow a user to input at least one of estimated misalignment, eye information, and lens information; and a display comprising a graphical user interface to display selected tIOL information, wherein the processing circuitry is operably coupled to the input apparatus and the display and further configured to display the selected tIOL information.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 5 illustrates an example of a lens calculator implementation of split-the-difference without posterior corneal astigmatism inclusion.

FIG. 6 illustrates an example of a lens calculator implementation of split-the-difference with posterior corneal astigmatism inclusion based on Abulafia-Koch correction.

FIG. 7 illustrates use of another example tIOL calculator that uses split-the-difference with posterior corneal astigmatism inclusion.

FIG. 8 illustrates example split-the-difference calculations for tIOLs from another illustrative lens calculator.

FIG. 9 illustrates an example of another lens calculator that provides different step sizes than those of lens calculators described earlier above.

DETAILED DESCRIPTION

This disclosure generally relates to various embodiments of selection of toric intraocular lenses (tIOLs) for use in treating astigmatism. When selecting a particular tIOL for astigmatism correction, parameters such as cylinder of the lens at the corneal and IOL plane, and the anticipated overcorrection and undercorrection of the selected lens at the corneal plane are considered. Surgeons may use toric calculators to select the correct tIOL for a given patient astigmatism. However, toric calculators have historically avoided overcorrection based on misunderstandings of the optical principles underlying image formation and perception, leading to inaccuracies in lens selection. More recently, some toric calculators have migrated to a "split-the-difference" strategy where overcorrection is accepted if the residual provided by the overcorrecting tIOL is less than that of the undercorrecting one. However, the decision of overcorrecting at an apparently favorable residual may be more subtle than originally considered.

Methods and apparatuses according to embodiments provide an improved and enhanced decision-making process on deciding when an overcorrecting tIOL should be selected over an undercorrecting tIOL. As described herein, residual astigmatism increases faster in the presence of overcorrection as compared to undercorrection. An overcorrecting tIOL residual, which may be smaller than a corresponding undercorrecting residual when zero misalignment is present, will rise faster with rising misalignment. As misalignment increases, the misalignment will reach, and then exceed, the slower rising undercorrecting residual, at which point the overcorrecting tIOL will cease to be the optimal choice. Because misalignment is inevitable and can arise from a variety of predictable and unpredictable reasons, various embodiments described herein can implement overcorrecting by selecting the overcorrecting astigmatism at a more realistic degree of misalignment, rather than at zero misalignment.

Figure 1:
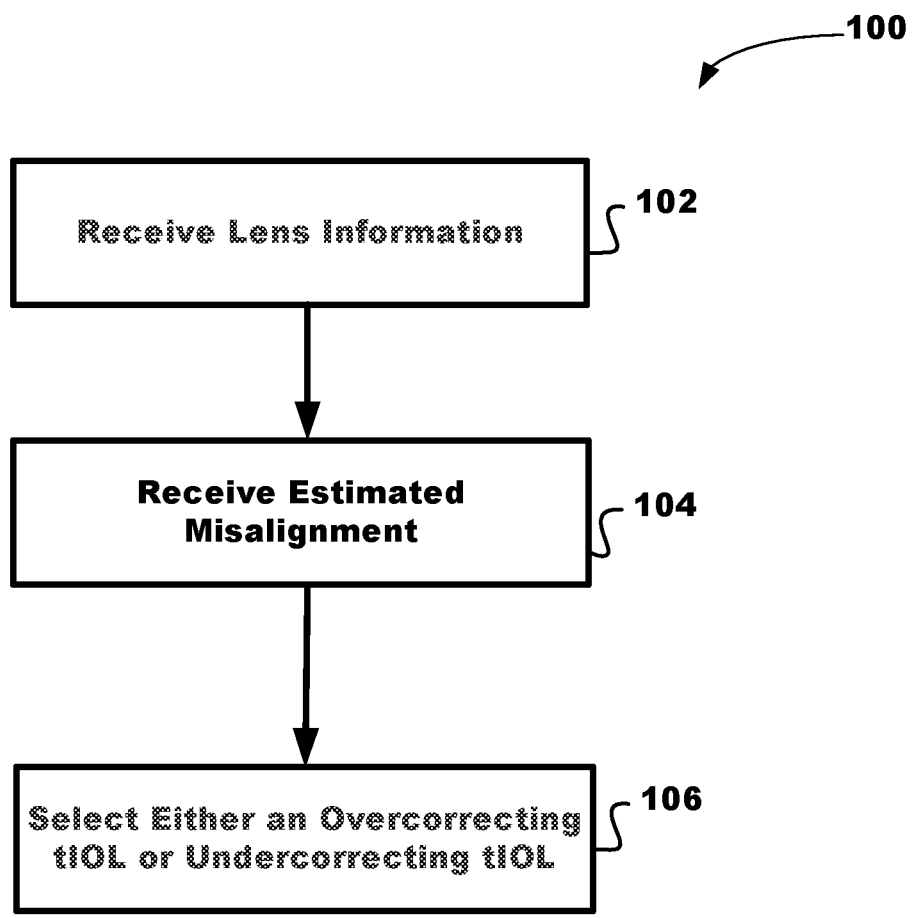
FIG. 1 illustrates an example method for selecting a toric intraocular lens in accordance with embodiments.

FIG. 1 illustrates an example method 100 for selecting a tIOL in accordance with embodiments. The method 100 can be implemented by any element of a computing pparatus or system such as a described herein with respect to a computing system 1100 of FIG. 11, which includes, for example, processing circuitry 1104 and an interface 1108.

The method 100 can begin with operation 102 with the processing circuitry 1104 receiving over, for example, interface 1108, lens information for an overcorrecting tIOL and an undercorrecting tIOL for an eye to be treated with the selected tIOL. Lens information can include, for example, one or more of the following: the step increment in diopter between two successive tIOLs, at the corneal plane and at the IOL plane, the overcorrection and undercorrection, in diopters, of the overcorrecting tIOL and the undercorrecting tIOL at the corneal plane and at the IOL plane, the cylinder of the overcorrecting tIOL and the undercorrecting tIOL at the corneal plane and the IOL plane, values for determining pairs of undercorrecting and overcorrecting tIOLs, and other values described with reference to FIG. 3 and further in the illustrative examples of FIGS. 5-10.

Figure 4:
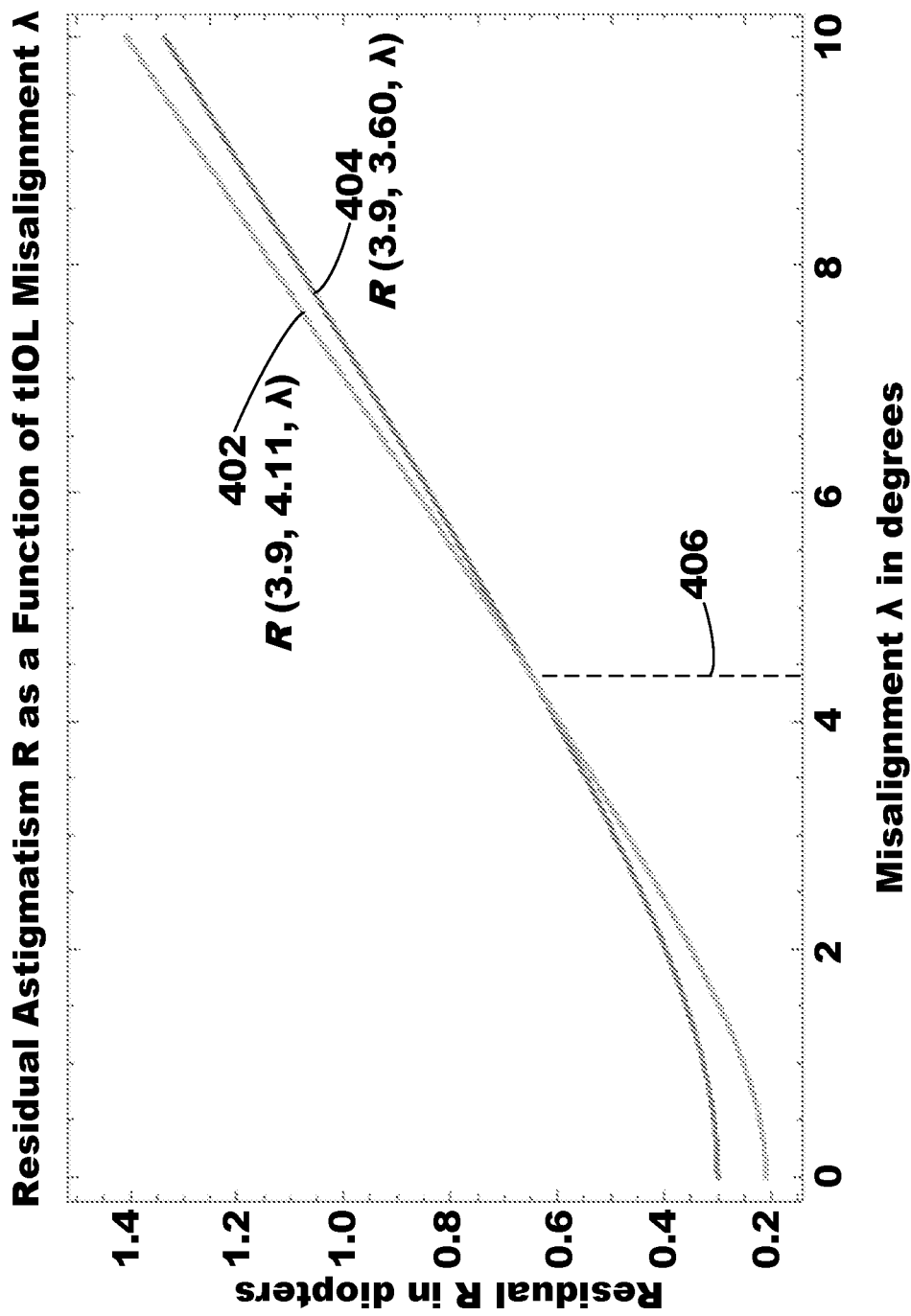
FIG. 4 illustrates residual astigmatism as a function of tIOL misalignment.

The method 100 can continue with operation 104 with the processing circuitry 1104 receiving an estimated misalignment. The estimated alignment can be received from, for example, local or remote storage, or user input. Estimated misalignment is described with reference to FIG. 4 and associated text later herein, and in particular reference numeral 406 (FIG. 4). The estimated misalignment is the estimated misalignment of the to-be-implanted tIOL with respect to the astigmatism of the cornea following the completion of the surgical procedure. The corneal astigmatism to be corrected results from a combination of anterior and posterior astigmatism as well as surgically induced astigmatism. These quantities are either measured or estimated with a significant uncertainty of such measurements/ estimates resulting in a corresponding uncertainly not only on the magnitude of the final corneal astigmatism to be corrected but also its orientation/direction. Cyclotorsion and tIOL misalignment and rotation are additional sources of uncertainly on the coincidence of alignment of tIOL and corneal astigmatism. Equations further defining estimated alignment are provided in Eq $\chi$ and Eq $\chi$ HΩBU provided later herein. In some embodiments, method 100 can include the processing circuitry 1104 receiving eye information for an eye to be treated by the selected tIOL and determining the estimated misalignment based on the eye information and the lens information.

The method 100 can continue with operation 106 with the processing circuitry 1104 selecting one of the overcorrecting tIOL and the undercorrecting tIOL based on lens information for the overcorrecting tIOL and the undercorrecting tIOL and the estimated misalignment. Details for example methods and algorithms for selecting one of the overcorrecting and undercorrecting tIOL are provided below.

In some embodiments, operation 106 can include determining a minimum astigmatism to be overcorrected. This minimum astigmatism can be calculated according to Eq $A_{min}$ or Eq $A_{min}'$, for example, provided in detail later herein. In at least these embodiments, the minimum astigmatism is based in addition to the eye measurement information and surgically induced astigmatism (SIA), on the estimated misalignment and on toric lens information. In at least these embodiments, the processing circuitry 1104 can select the overcorrecting tIOL if the thus computed value for the minimum astigmatism is less than the astigmatism of the eye to be treated with the selected tIOL.

In some embodiments, method 100 can include the processing circuitry 1104 determining a maximum astigmatism to be overcorrected. In at least some embodiments, the maximum astigmatism can be based on the estimated misalignment. The processing circuitry 1104 can determine the maximum astigmatism to be overcorrected using, for example, EQ $\Omega_{max}$ as described in more detail later herein.

In some embodiments, the lens information can include an overcorrection value that indicates an amount of overcorrecting that would occur with the overcorrecting tIOL. For example, "Methods for HΩBU calculators," described in more detail later herein, can select lens based on the overcorrection value that indicates an amount of overcorrecting that would occur with the overcorrecting tIOL. In at least these embodiments, the processing circuitry 1104 can select the tIOL by determining a maximum astigmatism to be overcorrected and selecting the overcorrecting tIOL if the overcorrection value is less than the maximum astigmatism to be overcorrected. In other embodiments, the processing circuitry 1104 can determine a minimum astigmatism to be overcorrected and select the overcorrecting tIOL if the minimum astigmatism is less than the astigmatism of the eye to be treated with the selected tIOL.

All headings provided herein are for the convenience of the reader and should not be used to limit the meaning of any text that follows the heading, unless so specified.

The terms "comprises", and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

EXAMPLES

An analysis is presented for surgical situations in which both mismatch and misalignment exist. The analysis below determines the point at which overcorrection and undercorrection residuals coincide, thereby predicting the degree of overcorrection with a tIOL that will best improve a patient's astigmatism. The method is illustrated for tIOLs used in surgical practice.

Results: the minimum astigmatism appropriate to overcorrect with a tIOL is given by, $$A_{min} = \frac{m}{\cos 2\chi},$$

where m is the midpoint threshold used by "split-the-difference" algorithms in addition to other algorithms in accordance with various embodiments, and $\chi$ is the estimate of tIOL misalignment due to all causes. Correspondingly, the maximum overcorrection, $\Omega_{max}$, that should be attempted is $$\boxed{\Omega_{max} = \frac{\sigma}{2\tau}[1 - \gamma(2n - 1)]}$$

where $$\alpha = \frac{\sigma}{\tau}$$

is the dioptric step at the corneal plane, with $\sigma = H - B$, where $H = n\sigma$ is the cylinder of the overcorrecting tIOL and $B = (n-1)\sigma$ is the cylinder of the undercorrecting tIOL, both at the IOL plane, $\tau$ is the toricity ratio and $\gamma$ relates to the angle of misalignment $\chi$ by $$\gamma = \frac{1}{\cos 2\chi} - 1$$

which can be approximated by $$\gamma \approx \left(\frac{\chi_{deg}}{40}\right)^2$$

where $\chi_{deg}$ refers to the angle measure in degrees. $\Omega_{max}$ factors elegantly in the product of $$\frac{\alpha}{2},$$

the (ideal) midpoint correction for perfect alignment, by the bracketed term, representing the percent reduction of the ideal value in a realistic surgical situation with estimated misalignment $\chi$. To illustrate: an eye of average dimensions ($\tau \sim 3/2$) and tIOLs from major manufacturers ($\sigma = 3/4$), with A=2.35 D dictating n=5. For a misalignment of 10° $\Omega_{max} \cong 0.10$ D is the maximum overcorrection that should be accepted, significantly smaller than the midpoint $$\frac{\alpha}{2} = \frac{\sigma}{2\tau} = 0.25 \text{ D},$$

recommended by many current tIOL calculators.

Figure 2:
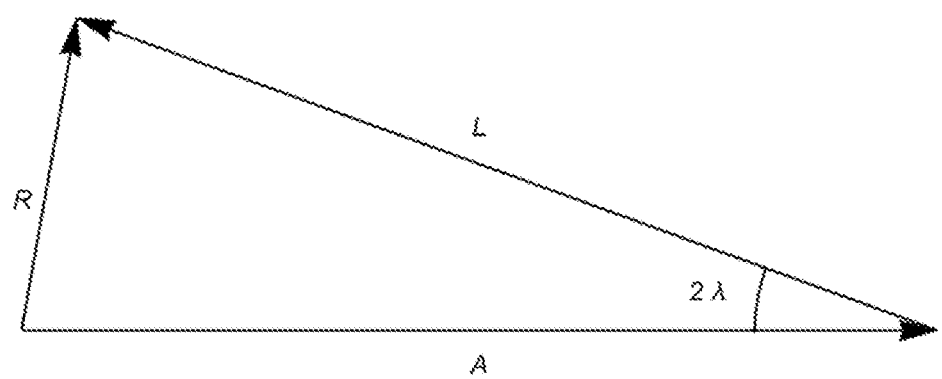
FIG. 2 is a representation of astigmatism A with an attempted correction L that has rotated by an angle λ with respect to the intended meridian, with a residual astigmatism R.

Three figures are provided to guide the reasoning and the derivations that follow. First, FIG. 2 is a triangle representation of astigmatism A with an attempted correction L that is misaligned by an angle λ with respect to the intended meridian, with a residual astigmatism R. The geometric representation and residual calculation are based on a triangle with an angle 2λ between the sides, A and L. From elementary geometry an "SAS" (side angle side) triangle is uniquely determined and therefore both the residual astigmatism and its meridian are computable using the law of cosines as in Equation (1):

$$R^2(\lambda) = A^2 + L^2 - 2\ A\ L\ \cos 2\lambda = A^2 + L^2 - 2\ A\ L\ C \quad (1)$$

where cos 2λ=C.

Figure 3:
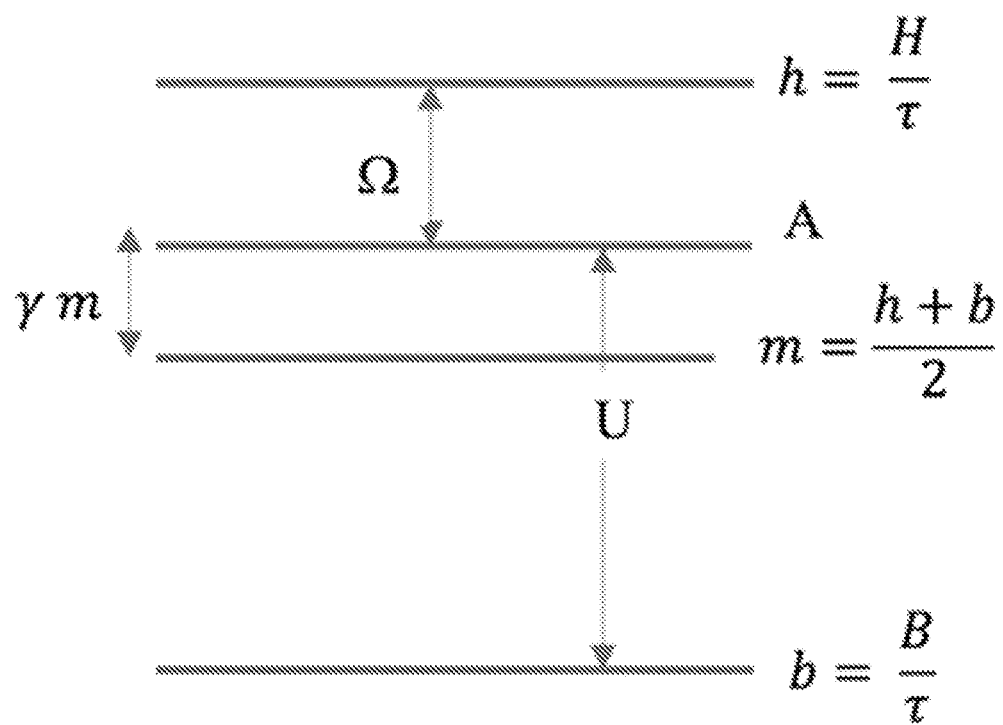
FIG. 3 illustrates astigmatism levels at the corneal plane.

As illustrated in FIG. 3, the astigmatism, A, to be corrected at the corneal plane is bracketed or "sandwiched" between a high value, h diopters, and a "below" value, b diopters, both at the corneal plane, corresponding to overcorrecting tIOLs with tIOL plane values H diopters and B diopters, respectively. m is the midpoint, or average of h and b. Ω is the amount of overcorrection when H (and correspondingly h) is chosen and U the amount of undercorrection when (B and correspondingly b) is chosen. γ is the fractional increment of A with respect to m.

IOL plane values are related to corneal plane values by the toricity ratio, τ. H and B are assumed to be separated by a discrete value or "step" of σ diopters (which can also be referred to as the "first quantization of astigmatism correction"). Finally, we designate the ratio $$\alpha = \frac{\sigma}{\tau}$$

as the dioptric step at the corneal plane. In other words, we have, $$H - B = \sigma \quad (2a)$$

$$h = \frac{H}{\tau} \quad (2b)$$

$$b = \frac{B}{\tau} \quad (2c)$$

Combining Equations (2a), (2b) and (2c) we obtain, $$h - b = \frac{\sigma}{\tau} \quad (2d)$$

We also introduce the midpoint, m, $$m = \frac{h + b}{2} \quad (2e)$$

and the value n, $$n = \frac{H}{H - B} = \frac{h}{h - b} \quad (2f)$$

which is not necessarily, but often turns out to be, an integer.

Combining Equations (2a) and (2f), we can write, $$H = n\ \sigma \quad (2g)$$

And similarly, $$B = (n-1)\sigma \quad (2h)$$

And combining with Equations (2a) and (2b) and $$\alpha = \frac{\sigma}{\tau}$$

we can write, $$h = n\frac{\sigma}{\tau} = n\alpha \quad (2i)$$

And, $$b = (n-1)\frac{\sigma}{\tau} = (n-1)\alpha \quad (2j)$$

From which we have, $$m = \left(n - \frac{1}{2}\right)\frac{\sigma}{\tau} = \left(n - \frac{1}{2}\right)\alpha \quad (2k)$$

Note also that, $$U + \Omega = \alpha \quad (2l)$$

If we express the various astigmatic quantities in units of $$\alpha = \frac{\sigma}{\tau}$$

we can simply visualize the levels of overcorrection, undercorrection tIOLs, and midpoint as expressed by n, n−1, and n−1/2.

Using Equation 1 we can calculate the residual astigmatism for any under or overcorrection of an astigmatism, A, and display their variation as a function of the degree of misalignment, λ.

FIG. 4 illustrates residual astigmatism as a function of tIOL misalignment. Graph 400 includes curve 402, which represents astigmatism A=3.9 D with an initially favorable overcorrecting tIOL of 4.11 D (residual 0.21 D). Curve 404 represents an undercorrecting tIOL of 3.60 D (residual 0.30 D), all at the corneal plane. Beyond misalignment by an angle λ=χ~4 degrees, the residual associated with overcorrection (Curve 402) equals then starts exceeding the residual of the undercorrection.

We can now formalize this approach to arrive at exact results as well as useful clinical approximations.

The residual astigmatism resulting from undercorrecting A diopters of astigmatism with b diopters, (b<A), will satisfy equation (1) and thus we will have:

$$R_b^2 = A^2 + b^2 - 2\ A\ b\ C \quad (3a)$$

Similarly, the residual astigmatism resulting from an overcorrection of A diopters with h diopters, (h>A), will also satisfy equation (1) and thus we will also have:

$$R_h^2 = A^2 + h^2 - 2\ A\ h\ C \quad (3b)$$

Equal residuals for over and undercorrection occur at a crossing angle $\lambda=\chi$ (e.g., crossing angle 406) and is obtained by equating Equations (3a) and (3b), resulting in $$h+b=2\,A\,C \quad (3c)$$

Writing in terms of $$m=\frac{h+b}{2},$$

the midpoint between h and b, we now have for the minimum astigmatism to be overcorrected, $$A_{min}=\frac{m}{\cos 2\chi} \quad \text{(Eq } A_{min}\text{)}$$

which can also be written as, $$A_{min}=\left(n-\frac{1}{2}\right)\alpha\frac{1}{\cos 2\chi} \quad \text{(Eq } A'_{min}\text{)}$$

because $m=(n-1/2)\alpha$.

Note that $A_{min} \geq m$ where the midpoint $m=(n-1/2)\alpha$ is the typical value used for a "split the difference" algorithm that selects based on a middle value. Because $\cos 2\chi \leq 1$, A will be larger than m and will continue to grow with increasing $\chi$ throughout the clinically realistic range. To illustrate, for astigmatism 1.30 D, bracketed by b=1.00 D and h=1.50 D, a split-the-difference approach would suggest that any A above m=1.25 D should be overcorrected. However, given an illustrative angle $\chi=10°$, $$A_{min}=\frac{m}{\cos 2\chi} \cong 1.33\ \text{D},$$

and astigmatism up to 1.33 D should continue to be undercorrected.

To express the crossing angle $\chi$ as a function of A, $\sigma$, and $\tau$ equation Eq $A_{min}$ can be written as:

$$\chi=\frac{1}{2}\arccos\frac{m}{A} \text{ with } A \geq m \quad \text{(Eq } \chi\text{)}$$

For a given eye characterized by (A, $\tau$) and a given manufacturer's tIOLs offerings characterized by (n, $\sigma$) the crossing angle $\chi$ is determined by (Eq $\chi$).

Using equation (2a) to (2l) $\chi$ can be written in terms of H,$\Omega$,B,U:

$$\chi=\frac{1}{2}\arccos\frac{1}{2}\frac{(H+B)(\Omega+U)}{HU+B\Omega} \quad \text{(Eq } \chi \text{ H}\Omega\text{BU)}$$

Two questions may be described as being answered by (Eq $\chi$) and (Eq $A_{min}$): First, (Eq $\chi$) answers the question of determining the crossing angle of over and undercorrecting tIOLs selected from a sequence of tIOLs characterized by (n, $\sigma$) for astigmatism A in an eye characterized by (A, $\tau$). (Eq $\chi$ H$\Omega$BU) allows for this calculation to be done without direct knowledge of A but rather through values returned by available toric calculators. Once that angle is determined, it can be decided if such an angle is adequate or too small and from this determination the corresponding degree of overcorrection can be accepted or rejected. In the example illustrated by FIG. 4, an astigmatism of 3.90 D is to be corrected and, at the corneal plane, the overcorrecting and undercorrecting tIOL powers are given by 4.11 D and 3.60 D respectively, yielding $$m=\frac{4.11+3.60}{2} \text{ and } \chi=\frac{1}{2}\arccos\frac{m}{A} \cong 4.4°$$

consistent with the graphical representation in FIG. 4. The clinical question then is whether the preoperative and intraoperative measurements including all estimates of astigmatism (anterior, posterior, SIA, cyclotorsion, alignment, other) and potential postoperative rotation combine to about 4 degrees or less, in which case the overcorrection should be accepted and otherwise the undercorrection should be preferred.

(Eq $A_{min}$) on the other hand, takes as an input of an estimated crossing angle $\chi$ in addition to the other parameters. In methods according to embodiments, this input estimate of $\chi$ is presumed to be the estimate of the degree of misalignment from all causes. A value of $A_{min}$ is then computed at or below which only undercorrection should be accepted. As an example, given $\chi=5°$ and using the same value of m, $$A_{min}=\frac{m}{\cos 2\chi} \cong 3.91\ \text{D}.$$

This signifies that in the presence of a misalignment of 5°, the least astigmatism to be corrected should be 3.91 D, a value consistent with the previous example and illustrated in FIG. 4. It is possible to graph corresponding values of A and $\chi$ and use such graph as a lookup table according to other examples provided later herein.

In some embodiments, the degree of overcorrection is dealt with directly, because some calculators do not explicitly present the value of total corneal astigmatism. This can be the case, for example, because an undisclosed contribution of posterior astigmatism is included.

As indicated in FIG. 3, the overcorrection $\Omega$ is given by $\Omega=h-A$ and using Eq $A_{min}$ the below is derived:

$$\boxed{\Omega_{max}=\frac{\alpha}{2}[1-\gamma(2n-1)]} \quad \text{(EQ } \Omega_{max}\text{)}$$

with, $$\gamma=\frac{1}{\cos 2\chi}-1 \quad \text{(EQ } \gamma\chi\text{)}$$

As described in more detail later herein, $\gamma$ can be approximated as:

$$\gamma \approx \left(\frac{\chi_{deg}}{40}\right)^2 \quad (A3)$$

Note that $$\frac{\alpha}{2} = \frac{\sigma}{2\tau}$$

being the midpoint correction between h and b, $\Omega_{max}$ is lesser than that midpoint value for any positive values of A and $\chi$. The reduction from that midpoint threshold is proportional to A (via n) and to $\chi^2$ for most realistic values of the misalignment $\chi$. In other words, the larger the misalignment and the higher the amount of astigmatism to be corrected, the smaller the allowed overcorrection, the optimal degree of overcorrection that should be sought potentially reaching zero or a negative value, precluding any consideration of overcorrection.

Taking the limit A→0 or $\chi$→0, we have $$\Omega = U = \frac{\alpha}{2} = \frac{\sigma}{2\tau},$$

the midpoint or "split-the-difference" solution.

As an example consistent with the previous examples, given $\chi=5°$ and using the approximation from equation (A3) above to compute $$\gamma = \left(\frac{1}{8}\right)^2$$

and with n=8, σ=0.75 D and $\tau \cong 1.46$ we have $$\Omega_{max} = \frac{\alpha}{2}[1 - \gamma(2n-1)] = 0.257[1 - 0.23] \cong 0.20 \text{ D}.$$

This answer is consistent with the one obtained following the $A_{min}$ method since $A_{min}+\Omega_{max}=h$, or 3.91+0.20=4.11. This signifies that no larger overcorrection than 0.20 D should be accepted in this context if the misalignment is estimated at $\chi=5°$. We can observe that the bracketed value [1-0.23] represents the percent reduction of the admissible overcorrection as compared to the "split-the-difference"

$$\frac{\alpha}{2}$$

value corresponding to the perfect alignment case $\chi=0°$.

An example method to determine a degree of overcorrection in accordance with embodiments. Either equation (Eq $A_{min}$) or (EQ $\Omega_{max}$) can be used to determine an appropriate degree of overcorrection for a given estimate of misalignment $\chi$, at which the residual curves intersect, and overcorrection is no longer advantageous.

Either (Eq $A_{min}$) and (EQ $\Omega_{max}$) can be executed by, for example, processing circuitry 1104 described later herein with respect to FIG. 11. As a result of execution of one of these equations, a tIOL can be selected based on the maximum allowable overcorrection. The steps outlined can be done de novo or obtained or determined from values provided by an existing toric calculator, even though that calculator may be recommending a suboptimal choice.

De Novo Methods for Lens Selection

In either the de novo $A_{min}$ or de novo $\Omega_{max}$ method, the inputs can include:

1) biometric specification for an eye and planned incisions with corresponding SIA allowing for total corneal astigmatism A and toricity ratio τ to be determined. This information depends on measurements performed on the individual eye, for example.
2) a sequence or subsequence (minimum 2) of tIOLs that allow for the step σ, to be specified in diopters, as well as n, n being a single value or a sequence of possible values. This is done via equations (2a) and (2f). This information depends on tIOLs made available by a manufacturer.
3) an estimate or computation of the crossing angle of misalignment $\lambda=\chi$ due to all causes. This estimate depends on reliability of instrumentation and models used to estimate various measurements and previous experience.

de novo $A_{min}$

1) Determine a by selection of manufacturer's sequence or sub-sequence of tIOLs (Eq. 2a).
2) Determine τ by measuring the eye's axial length, K values, and any other biometric variables and using manufacturers' recommendations or/and using an appropriate formula or nomogram. Average τ is about 1.30-1.50 depending on type of IOL and increasing with increasing axial length and corneal curvature.
3) Determine $$\alpha = \frac{\sigma}{\tau}$$

the dioptric step at the corneal plane.

4) For astigmatism A to be corrected at the corneal plane, calculate n by determining H as the smallest value of a tIOL larger than the product τA, and determining B as the largest value of a tIOL smaller than the product τA. Then use $$n = \frac{H}{H-B}.$$

5) Most manufacturers often provide a sequence given by H=n σ, where n takes integer values, and we then simply have $$n = \left\lceil \frac{1}{\alpha}A \right\rceil.$$

Select the corresponding candidate tIOLs, B=(n-1)σ and H=n σ, undercorrecting and overcorrecting A. See for example Table 1 for an example of tIOLs sequence.

6) Estimate $\chi$ based on historical data or based on the estimate of all contributions to misalignment in a surgical case, then calculate $$\gamma = \frac{1}{\cos 2\chi} - 1$$

or use the approximation $$\gamma \approx \left(\frac{\chi_{deg}}{40}\right)^2$$

7) Substitute the values obtained in steps 1 through 5 in $$A_{min} = \left(n - \frac{1}{2}\right)\alpha \frac{1}{\cos 2\chi} = \left(n - \frac{1}{2}\right)\alpha(\gamma + 1) = m + \gamma m.$$

So $A_{min}$ compared to the "split-the-difference" methods shifts from m to m+γm as indicated in FIG. 3. Given that an approximation is possible for γ, in some example embodiments it may be practical to use γ. For example for a crossing angle of 8 degrees, γ is 1/25 etc.

8) Overcorrect A with H if and only if A>$A_{min}$, otherwise choose B=H−σ.

de novo $\Omega_{max}$

1) Determine σ by selection of manufacturer's sequence or sub-sequence of tIOLs (Eq. 2a).
2) Determine τ by measuring the eye's axial length, K values and any other biometric variables and using manufacturers' recommendations or/and using an appropriate formula or nomogram. An example average τ is about 1.30-1.50 and can depend upon type of IOL and increasing with increasing axial length and corneal curvature.
3) Determine $$\alpha = \frac{\sigma}{\tau}$$

the dioptric step at the corneal plane.

4) For astigmatism A to be corrected at the corneal plane, calculate n by determining H as the smallest value of a tIOL larger than the product τA, and determining B as the largest value of a tIOL smaller than the product τA. Then use $$n = \frac{H}{H - B}.$$

5) Most manufacturers have a sequence given by H=n σ, n integer and we then simply have $$n = \left\lceil \frac{1}{\alpha} A \right\rceil.$$

Select the corresponding candidate tIOLs, B=(n−1)σ and H=nσ, undercorrecting and overcorrecting A. See for example Table 1 for an example of tIOLs from a specific manufacturer.

6) Estimate χ based on historical data or based on the estimate of all contributions to misalignment in a surgical case, then calculate $$\gamma = \frac{1}{\cos 2\chi} - 1$$

or use the approximation $$\gamma \approx \left(\frac{\chi_{deg}}{40}\right)^2$$

7) Substitute the values obtained in steps 1 through 5 in $$\Omega_{max} = \frac{\alpha}{2}[1 - \gamma(2n - 1)]$$

8) Overcorrect A with H if and only if $$\Omega = \frac{H}{\tau} - A < \Omega_{max},$$

otherwise choose B=H−σ

Note that the astigmatism, A, to be corrected is the corneal astigmatism resulting from all contributions, including anterior astigmatism, posterior astigmatism and astigmatism induced by surgical incisions. The astigmatism A can be equivalent to the residual astigmatism that would result in case a non-toric intraocular lens is used. Some toric calculators display such a value for astigmatism A? and corresponding options for tIOL choices and corresponding residuals. Methods according to embodiments are executed under the assumption that an appropriate methodology for computing A is provided. It is also noted that available methods show lack of an accepted standard and that the variety of methods that yield different results, introducing uncertainties that contribute to both mismatch and misalignment. The lack of an accepted standard can, in turn, arise from uncertainty as to whether to include SIA in determining misalignment, how much posterior astigmatism to include, orientation of surgeon relative to patient, position of the patient, etc.

Some available calculators will provide a set of values amongst those shown in FIG. 3 and satisfying Equations (2a) to (2l) The methods provided below are directed to take into account overcorrection Ω, undercorrection U and corresponding tIOLs cylinders, H and B, at the IOL plane. These values can be provided by calculators referred to herein as "HΩBU calculators" and algorithms based on inputs from HΩBU calculators are provided below.

HΩBU

For H,Ω,B,U being given in diopters:

Based on Ω

1) Determine α=Ω+U, the dioptric step at the corneal plane
2) Calculate n by $$n = \frac{H}{H - B}$$

3) Estimate $\chi$ based on historical data or all contributions to misalignment, then calculate $$\gamma = \frac{1}{\cos 2\chi} - 1 \text{ or use } \gamma \approx \left(\frac{\chi_{deg}}{40}\right)^2$$

4) Substitute the values obtained in 1) to 3) in $$\Omega_{max} = \frac{\alpha}{2}[1 - \gamma(2n-1)]$$

5) Overcorrect with H if and only if $\Omega < \Omega_{max}$, otherwise choose B Based on A
1) Through 3) as above
4)

$$A_{min} = \left(n - \frac{1}{2}\right)\alpha \frac{1}{\cos 2\chi}$$

5) Overcorrect H if and only if $A_{min} < A$ (with A provided by calculator or evaluated by $$A = \frac{1}{H-B}(B\Omega + HU),$$

else use B

Common tIOLs and Examples

A common situation with tIOLs in increments of $\sigma$ diopter at the IOL plane is that of a "$T_n$" sequence with $\sigma=3/4$ diopter (some examples described later herein are such that $T_n = \sigma(n-1)$). A very common clinical scenario is the one where n=3, resulting in a T3/T4 pair choice, for which T3 corrects 1.50 diopters and T4 corrects 2.25 diopters respectively at the IOL plane with an approximate correction for an average eye (assuming a toricity ratio of about 1.50) of 1 diopter and 1.50 diopters at the corneal plane. An eye of axial length 24 mm and average K of 44 diopters would correspond to such a toricity ratio but depending on the toricity ratio the corresponding cylinder at the corneal plane may potentially vary by less than half a diopter for a T3 and up to or exceeding 2 diopters for higher $T_n$ as indicated in Table 1, where the $T_n$ sequence of tIOLs characterized by a sequence $T_n=0.75(n-1)$ at the tIOL plane and corresponding cylinder values at the corneal plane vary with toricity ratio. In Table 1 below, $\sigma=0.75$ D and $n=\{3,4,5,6,7,8,9\}$.

TABLE 1

| T | IOL Plane | Avg Cornea Plane | Min Cornea Plane | Max Cornea Plane |
|---|---|---|---|---|
| 3 | 1.50 | 1.03 | 0.83 | 1.25 |
| 4 | 2.25 | 1.54 | 1.25 | 1.88 |
| 5 | 3.00 | 2.06 | 1.67 | 2.50 |
| 6 | 3.75 | 2.57 | 2.08 | 3.13 |
| 7 | 4.50 | 3.08 | 2.50 | 3.75 |
| 8 | 5.25 | 3.60 | 2.92 | 4.38 |
| 9 | 6.00 | 4.11 | 3.33 | 5.00 |

Given a "$T_n$" sequence with $\sigma=3/4(0.75)$ and a near average eye with $\tau=3/2(1.50)$ we have the following simplified expression for $\Omega_{max}$:

$$\Omega_{max} = 1/4[1-\gamma(2n-1)] \qquad \text{(EQ } \Omega_{max} \text{ simple)}$$

where $\{n=3,4,5,6,7,8\}$

For $\gamma=0$, the trivial no misalignment case, the expected value of ¼ diopter is the point at which overcorrection and undercorrection yield equal residual astigmatism. Generally, however, $\gamma$ will be different than zero and the resulting $\Omega_{max}$ will also depend on the degree of attempted astigmatism correction via n.

Consider the example of an astigmatism of 1.30 diopter, potentially correctable by a T3 tIOL with cylinder 1.00 at the corneal plane, or a T4 with 1.50 diopter at the corneal plane. The midpoint is 1.25 diopter and 1.30 is in excess of 0.05 diopters of the midpoint. This corresponds to a fraction $\gamma=0.05/1.25=1/25$. Substituting in equation(Eq $\lambda_{deg}$) we obtain an angle of 8 degrees. This means that overcorrection will continue to be advantageous up to a misalignment/rotation of 8 degrees. If we anticipate a misalignment/rotation of 10 degrees (corresponding to $\gamma=0.064$) it would be preferable, then, to undercorrect. Indeed, proceeding with "Method $\Omega_{max}$" as described earlier herein and substituting $\gamma=0.064$ and $n=3$ in equation $\Omega_{max}$ we obtain $\Omega_{max}=0.17$ diopter. The maximum overcorrection to be allowed in this case should thus be 0.17, and the 0.30 undercorrection would be preferable to the 0.20 overcorrection.

Lookup tables or nomograms can be generated similar to that shown in, for example, Table 2. The first column of Table 2 provides the estimated misalignment/rotation angle of the toric IOL. The subsequent columns give, in diopters and for each pair of undercorrecting-overcorrecting tIOLs, the maximum amount of astigmatism that should be considered for overcorrection for each $T_n$ pair, for an "average" eye. Table 2 can serve as a practical reference for an "average eye" as indicated by the first row with entries of 0.25 D.

TABLE 2

| Est. misalignment | T3-T4 | T4-T5 | T5-T6 | T6-T7 | T7-T8 | T8-T9 |
|---|---|---|---|---|---|---|
| 0 | 0.25 | 0.25 | 0.25 | 0.25 | 0.25 | 0.25 |
| 5 | 0.23 | 0.22 | 0.22 | 0.21 | 0.20 | 0.19 |
| 10 | 0.17 | 0.14 | 0.11 | 0.07 | 0.04 | 0.01 |
| 15 | 0.06 | NA | NA | NA | NA | NA |

The first column gives the estimated misalignment/rotation angle of the toric IOL. As pointed out previously, all sources of misalignment errors need be included (uncertainly on axis measurement, SIA estimate error, posterior astigmatism uncertainty, marking, cyclotorsion, rotation of tIOL, etc.). The first row gives a constant value of 0.25 D indicating a perfect alignment, hardly a realistic assumption in clinical practice. Many surgeons can consider using an estimate around 10 degrees but both larger and smaller values can be considered based on a meticulous assessment of methods and historical surgical results. For 10 degrees, and even for much more optimistic estimates of 5 degrees, it is clear that the now conventional "split the difference" approach is far from ideal, especially as we correct higher degrees of astigmatism. The last row has only one minimum valid entry to T3-T4, and none corresponding to correction of higher degrees of astigmatism. This means that if the estimated misalignment is 15 degrees, only T3-T4 pair may potentially benefit from any overcorrection at all and only if this overcorrection is equal to or lesser than 0.06 D (for example it is still better in this case to undercorrect by 0.40 then to overcorrect by 0.10 D). All other pairs of tIOLs would always favor the undercorrecting tIOL no matter the discrepancy between the residuals. This recommendation is unlike, and preferable to, that of current toric calculators.

For 8 degrees of misalignment and using the approximate expression of $\gamma$ we get $$\left(\frac{8}{40}\right)^2 = \frac{1}{25} = \frac{4}{100}.$$

This value of $\gamma$ multiplied by $2n-1$ will be reduced from 1 to yield a percent reduction of the split-the-difference value $$\frac{\sigma}{2\tau}.$$

For $n=7$ we have a reduction of 52%, in other words the acceptable overcorrection should be less than half the one usually accepted for "split the difference" approaches.

Further Examples from Various Toric Calculators

Examples based on available tIOLs are provided below. These examples demonstrate the methods presented above and further demonstrate that the leading manufacturers of tIOLs have broadly adopted a split the difference approach where the overcorrection is always accepted until it becomes equal or superior to the undercorrection. As discussed earlier herein, this approach assumes zero misalignment and should be replaced by the methods of various embodiments that incorporate a realistic value of potential misalignment.

FIGS. 5 and 6 illustrate an illustrative lens calculator (for example, which could be provided by a lens manufacturer) implementation of split-the-difference with and without posterior corneal astigmatism inclusion.

In this standard algorithm (that assumes no posterior astigmatism contribution), we have $A=46.00-42.72=3.28$ D. This is a H$\Omega$BU calculator and we can apply the corresponding method.

Here $(H,\Omega,B,U)=(5.25,0.25,4.50,0.26)$ diopters. Determine $\alpha=\Omega+U=0.25+0.26=0.51$, the dioptric step at the corneal plane. Calculate n by $$n = \frac{H}{H-B} = \frac{5.25}{5.25-4.50} = 7.$$

Estimate $\chi$ based on historical data or all contributions to misalignment, then calculate $$\gamma = \frac{1}{\cos 2\chi} - 1$$

or use $$\gamma \approx \left(\frac{\chi_{deg}}{40}\right)^2.$$

We take $$\chi = 8^o \cdot \gamma \approx \left(\frac{8}{40}\right)^2 = \frac{1}{25} = \frac{4}{100} = 4\%.$$

Substitute the values obtained in 1) to 3) in $$\Omega_{max} = \frac{\alpha}{2}[1 - \gamma(2n-1)] = 0.255(100-52)\% = 0.12D$$

Overcorrect with H if and only if $\Omega<\Omega_{max}$, otherwise choose B. Since $\Omega=0.25$ D and $\Omega_{max}=0.12$ D we clearly have $\Omega>\Omega_{max}$ and overcorrection should be avoided and undercorrection selected.

Here we can also apply the $A_{min}$ method. Determine $$A_{min} = \left(n - \frac{1}{2}\right)\alpha \frac{1}{\cos 2\chi} = \left(7 - \frac{1}{2}\right)0.51 \frac{1}{\cos 16^o} \cong 3.45D.$$

This is larger than the value of $46-42.72=3.28$ D of the total astigmatism as entered, and again the overcorrection is not recommended in this circumstance.

Note that $A_{min}+\Omega_{max}\cong h=n\alpha$ as would be expected using methods according to various embodiments. For example, $A_{min}+\Omega_{max}\cong 3.45+0.12=7\times 0.51=3.57$. The two methods give the same result, as would be expected using methods according to various embodiments.

Note that the value suggested by methods in accordance with various embodiments, 0.12 D, is well below the value of 0.25 D that has been accepted by the calculator described with reference to FIG. 5.

The crossing angle for the values chosen by the calculator can be determined by applying Eq ($\chi$ H$\Omega$BU), which gives $\chi\cong 1.6^\circ$. If the surgeon is willing to accept the recommendation given, misalignment would need to be no more than about 1 degree, which may be an unrealistic expectation in most surgical cases.

The next example, shown in FIG. 6, uses the same calculator described above with reference to FIG. 5 with Abulafia-Koch correction. Methods according to this type of correction add a contribution of posterior astigmatism, which modifies the estimate of the magnitude of the astigmatism to be corrected and, generally, the astigmatism's meridian. The discrepancy between the axis when posterior astigmatism is taken into account and when it is not can introduce an uncertainty of several degrees on the final axis of the astigmatism to be corrected, thus further justifying the need for the methods according to various embodiments.

In this version of the calculator (on a slightly different example) and because of the inclusion of a contribution of posterior astigmatism (Abulafia-Koch regression), it is not immediately clear what is the amount of astigmatism being corrected. The methodology outlined can nevertheless be applied.

Here $(H,\Omega,B,U)=(4.50,0.25,3.75,0.26)$ diopters. Next, determine $\alpha=\Omega+U=0.25+0.26=0.51$, the dioptric step at the corneal plane. Next, calculate n by $$n = \frac{H}{H-B} = \frac{4.50}{4.50 - 3.75} = 6.$$

Estimate $\chi$ based on historical data or all contributions to misalignment, then calculate $$\gamma = \frac{1}{\cos 2\chi} - 1$$

or use $$\gamma \approx \left(\frac{\chi_{deg}}{40}\right)^2.$$

Taking $$\chi = 8°\gamma \approx \left(\frac{8}{40}\right)^2 = \frac{1}{25} = \frac{4}{100} = 4\%.$$

Substitute the values obtained in 1) to 3) in $$\Omega_{max} = \frac{\alpha}{2}[1 - \gamma(2n-1)] = 0.255(100 - 44)\% \cong 0.14\ D$$

Overcorrect with H if and only if $\Omega < \Omega_{max}$, otherwise choose B. Since $\Omega = 0.25$ D and $\Omega_{max} = 0.14$ D, $\Omega > \Omega_{max}$ and overcorrection should be avoided and undercorrection selected.

Applying the $A_{min}$ method with n=6:

$$A_{min} = \left(n - \frac{1}{2}\right)\alpha \frac{1}{\cos 2\chi} = \left(6 - \frac{1}{2}\right)0.51 \frac{1}{\cos 16°} \cong 2.92D$$

And compare to $$A = \frac{1}{H-B}(B\Omega + HU) = 2.81$$

and because $A_{min} > A$ the overcorrection is not recommended. $A_{min} + \Omega_{max} \cong h = n\alpha$ as expected, and $A_{min} + \Omega_{max} \cong 2.92 + 0.14 = 3.06 = 6 \times 0.51$.

The crossing angle for the values chosen by the calculator can be determined by applying Eq ($\chi H\Omega BU$). Using the example values here, $\chi \cong 1.7°$. Once again this may be an unrealistic expectation in most surgical cases.

Figure 7:
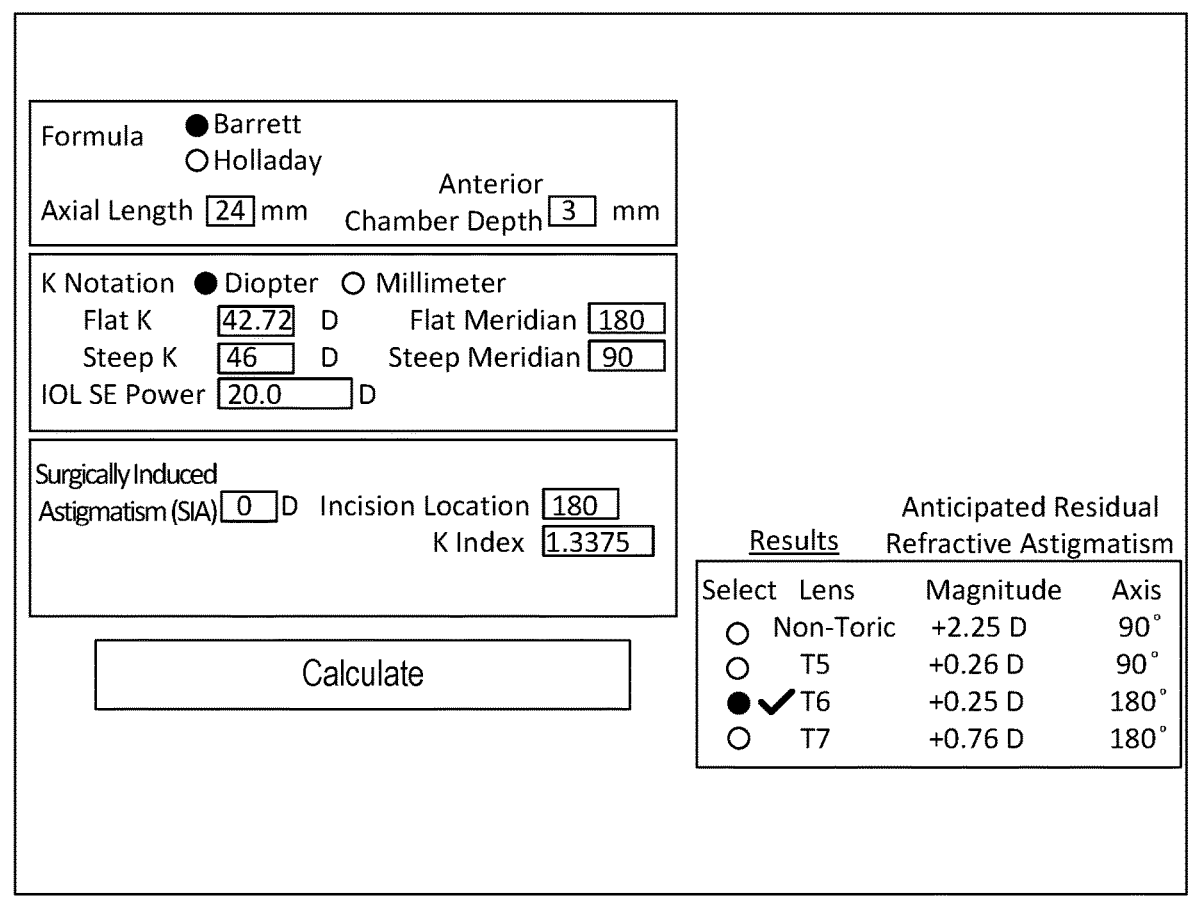

FIG. 7 illustrates the use of a second illustrative tIOL calculator (for example, which could be provided by a lens manufacturer) that uses split-the-difference with posterior corneal astigmatism inclusion. This example has identical corneal input values to that illustrated in FIG. 5 and utilizes the same step (which may be used by different tIOL manufacturers). This example illustrates that there is an overcorrection of 0.25 D selected in both cases. In this case with a drastically different selection of a T6, the value of n is 5. Notice also that we are given a value of the astigmatism residual in case of a non-toric which presumably coincides with the computed total corneal astigmatism once all contributions including posterior astigmatism are included. With n=5 we have $O_{max}[5, 0.75, 1.47, 8] = 0.16$ D where $O_{max}$ computes $\Omega_{max}$ as a function of the variables n, σ, τ, $\chi$ in that order.

Once again, we can see that the suggested correction with the split-the difference approach as provided by the illustrative calculator appears to overestimate the maximum overcorrection for realistic cases. Here too, we point out the fact that the suggested tIOL for the same eye has a different value even though it also overcorrects by a larger amount than the one we suggest. Indeed the tIOL calculator of FIG. 7 suggests a T7 tIOL with an overcorrected "flipped" residual of 0.18 D.

We can also determine the crossing angle for the values chosen by the calculator by applying Eq ($\chi H\Omega BU$) to get $\chi \cong 1.9°$, which is, again, unrealistic in most surgical cases.

FIG. 8 illustrates example split-the-difference calculations for tIOLs from a third illustrative calculator (for example, which could be provided by a lens manufacturer). The values for the tIOLs for this calculator are essentially identical to those of the tIOLs shown in Table 1, above. Calculation yields three possible solutions with the middle one presumably the recommended one. We can see in this example too (n=6) that the split-the-difference approach is used yielding 0.24 D overcorrection while the recommended Omax [6, 0.75, 1.50, 8]=0.14 D. The section entitled "Deducing toricity ratio and total corneal astigmatism," provided later herein, illustrates how to deduce the total corneal astigmatism and toricity ratio from the output given. We can easily calculate A=2.76 D according to equations provided below in "Deducing toricity ratio and total corneal astigmatism." We know $$m = \frac{\left(n - \frac{1}{2}\right)\sigma}{\tau} = 2.75D \text{ and } A_{min} = \frac{m}{\cos 2\chi} \cong 2.86D$$

for an angle $\chi=8°$. Clearly $A_{min} < A_{min}$ and the overcorrection should be rejected. Similarly, we calculate $$\Omega_{max} = \frac{\alpha}{2}[1 - \gamma(2n-1)] = 0.25 = (100 - 44)\% = 0.14D$$

and verify $A_{min} + \Omega_{max} = h = n\alpha$ as would be expected. Indeed, we have $A_{min} + \Omega_{max} \cong 2.86 + 0.14 = 3.00 = 6 \times 0.50$.

We can also compute the cross angle $\chi$ where the intersections of the overcorrection residual and undercorrection residual occur as $$\chi = \frac{1}{2}\arccos\frac{m}{A} = 0.5 arcos\frac{2.75}{2.76} = 2.4 \text{ degress},$$

so in order to accept the overcorrection provided by the calculator illustrated in FIG. 7, we should be confident that misalignment from all causes will not exceed about 2 degrees, a very unlikely eventuality as previously discussed.

FIG. 9 illustrates an example of an illustrative calculator (for example, which could be provided by a lens manufacturer) that provides different step sizes than those of calculators described earlier above with respect to FIGS. 5-8. While following the same general structure as exemplified by the above calculators, this calculator of FIG. 9 has a few significant differences that are worth noting before presenting an example of the methods used to handle overcorrection.

First, the value of the step is σ=0.50 D rather than the more common 0.75 D. The lenses suggested by this calculator provides a wider range of astigmatism correction in its tIOLs (up to 12 D of cylinder), corresponding to extending the values of n well beyond the value of 8 we have dealt with previously.

This example will also illustrate how to deal with a calculator that returns a single choice for the toric IOL, that choice itself being possibly associated with an overcorrection.

The example provided in FIG. 9 may be an extreme example that illustrates how the options for overcorrection narrow severely for high astigmatism. The solution offered in FIG. 8 by this calculator is for the following values: Kflat 42 D @180; Ksteep 49.36@90; Axial length 24 mm; ACD 3 mm; SIA=0 and no nomogram contribution to posterior astigmatism. It will be appreciated that corneal astigmatism is due to the cornea having two different curvatures (and thus optical powers) in two different meridians, most commonly 90 degrees apart. The meridian of lower curvature is designated as the flat meridian and its power can be designated by Kflat. The meridian of higher curvature is designated as the steep meridian and its power can be designated by Ksteep.

The example correction, therefore, is attempting to correct 7.36 D of astigmatism (i.e., A=7.36 D).

We choose these values to focus the discussion on the main emphasis of overcorrection and whether it should or should not be allowed. From the returned solution in FIG. 8 we can see that H=10 D, n=20, $\Omega$=0.13 D. We can determine i according to $$\tau = \frac{H}{h} = \frac{H}{A+\Omega} = \frac{10}{7.49} \cong 1.33 \cong 4/3.$$

We now have all the parameters needed to compute 1.) the minimum astigmatism that should be corrected for a given misalignment (e.g., 8 degrees), 2.) the maximum overcorrection that should be allowed for a given misalignment (e.g., 8 degrees) and 3.) the angle $\chi$ at which overcorrection would become less advantageous than undercorrection if we were to accept an overcorrection for the given value of A.

In sequence we have $$A_{min} = \left(n - \frac{1}{2}\right)\frac{\sigma}{\tau}\frac{1}{\cos 2\chi} \cong 7.6D.$$

Notice that this value exceeds h=7.49 D. This means that for an angle $\chi$=8° of misalignment there is no degree of overcorrection that is favored, no matter how small.

Computing the maximum overcorrection, we expect a similar result.

Indeed, the computation of $O_{max}$[20, 0.50, 1.334, 8] yields a negative result, again signaling that there is no allowable overcorrection for that degree of misalignment.

The simple physical interpretation of course is that the intersection of the overcorrection and the undercorrection curves has happened earlier than 8 degrees, just as represented in FIG. 4.

To determine the angle of intersection we use $$\chi = \frac{1}{2}\arccos\frac{m}{A}$$

with A≥m and we find $\chi$≅3.6<4°.

So, before a misalignment of 4° is reached, the overcorrection "advantage" will be lost. Until we are able to operate with that level of confidence in the alignment of the tIOL with the axis of the total corneal astigmatism, no such overcorrection should be attempted for that level of astigmatism.

Clinical Interpretation of Parameters $\gamma$ has a simple clinical interpretation. From Equation ($\gamma\chi$) and writing $\lambda$ for $\chi$ it is easily shown that $$\gamma = \frac{2\sin^2\lambda}{1 - 2\sin^2\lambda} \qquad (\gamma\lambda)$$

We thus have $$1 + \gamma = \frac{1 - 2\sin^2\lambda + 2\sin^2\lambda}{1 - 2\sin^2\lambda} = \frac{1}{1 - 2\sin^2\lambda} = \frac{1}{\cos 2\lambda} = \frac{1}{C}$$

Equation A reads $$A_{min} = \frac{m}{\cos 2\chi} = m(1 + \gamma)$$

Therefore, we have $$\gamma = \frac{A - m}{m} \qquad (A1)$$

In other words, $\gamma$ is the fractional excess of A with respect to the midpoint $$m = \frac{h + b}{2}$$

as seen in FIG. 3, and $\gamma$ has a simple clinically useful approximation. This equation relates $\lambda$ and $\gamma$ directly and provide clinically useful computational approximations:

Note that for $\lambda$=0, we will have $\beta$=$\gamma$=0, A=m and $\Omega$=U, as would be expected and shown in FIG. 3.

Inverting Equation ($\gamma\lambda$) we obtain $$\sin\lambda = \frac{1}{2}\sqrt{\frac{2\gamma}{1 + 2\gamma}} \qquad \text{(Eq lambda)}$$

with $$\sin\lambda = \frac{1}{2}\sqrt{\frac{2\gamma}{1 + 2\gamma}} \approx \frac{\sqrt{2}}{2}\sqrt{\gamma} \text{ (for } \gamma \ll 1\text{)}$$

Using the small angle approximation $\sin\lambda \approx \lambda$ and expressing the result in degrees, we obtain the very good approximation $$\lambda_{deg} \approx 40\sqrt{\gamma} \qquad (A2)$$

or

-continued $$\gamma \approx \left(\frac{\lambda_{deg}}{40}\right)^2 \quad (A3)$$

Note, as indicated in Table 3, that this approximation is excellent for the clinically relevant range of variables, as $\lambda_{deg}$ will not extend beyond 15 degrees in most clinical scenarios, and the approximate form can thus be used for rapid mental evaluation of undercorrection or overcorrection choices.

TABLE 3

Relationship between exact and approximate values of γ, the fractional excess astigmatism relative to the midpoint, as a function of $\lambda_{deg}$, the angle at which overcorrection residual equalizes undercorrection residual.

| $\lambda_{deg}$ | γ from exact expression (γλ) | γ from approximation (A2) |
|---|---|---|
| 0 | 0 | 0 |
| 5.0 | 0.0154 | 0.0156 |
| 10.0 | 0.064 | 0.063 |
| 15.0 | 0.15 | 0.14 |

Determining χ as a Function of A
(Eq χ) reads $$\chi = \frac{1}{2}\arccos\frac{m}{A} \text{ with } A \geq m$$

Figure 10:
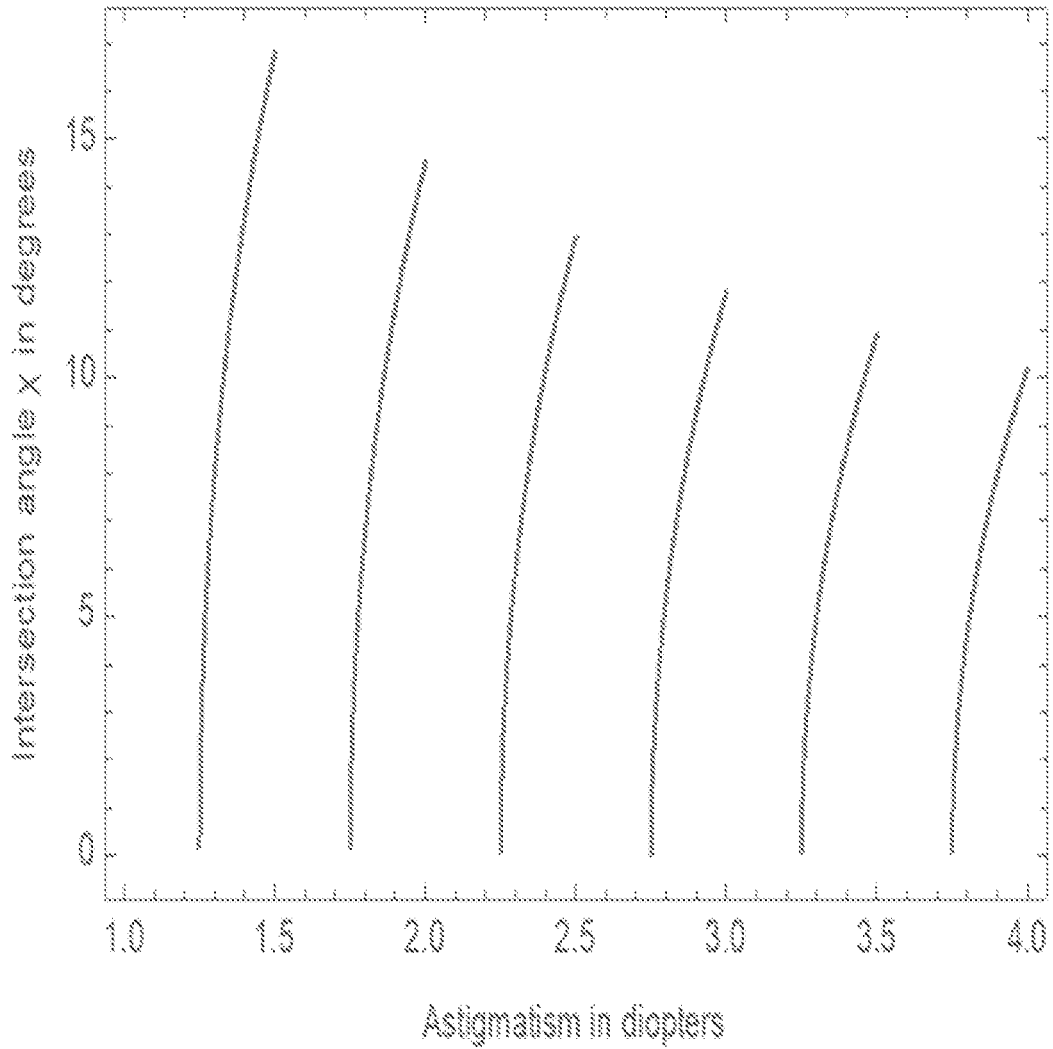
FIG. 10 illustrates crossing angle as a function of astigmatism.

Writing $$m = \frac{(2n-1)\sigma}{2\tau} \text{ with } n = \left\lceil \frac{\tau A}{\sigma} \right\rceil$$

we can now plot χ as a function of A as shown in FIG. 10.

For A from 1 D to 4 D for a given selection of σ and τ for example with σ=0.75 and τ=1.5, values most commonly encountered in clinical practice.

Note that when undercorrection<overcorrection we get no real solution for the angle, as expected. Also note that χ can be approximated by 40 √β with $$\beta = \frac{A - m}{A}.$$

So, if A is very close to mid point m, χ will be very small (this should be clear since when A=m, overcorrection and undercorrection are equal and "intersection" is at zero as the curves arise from the same point at zero misalignment). So very small differences favoring overcorrection are likely to disappear under minimum misalignment. The effect depends on m/A. Accordingly, it appears there is a step like behavior modulated by A.

Deducing Toricity Ratio and Total Corneal Astigmatism

It is possible to determine total corneal astigmatism and toricity ratio used from H, Ω, B and U as given for example by most toric calculators. From FIG. 2 we can see $$A + \Omega = \frac{H}{\tau} \text{ and } A - U = \frac{B}{\tau}$$

These two equations can be written in matrix form $$\begin{pmatrix} 1 & -H \\ 1 & -B \end{pmatrix} \begin{pmatrix} A \\ \frac{1}{\tau} \end{pmatrix} = \begin{pmatrix} -\Omega \\ U \end{pmatrix}$$

Both A and τ can be determined by inverting the matrix. This is done by inspection by exchanging the diagonal elements and flipping the signs of the non-diagonal elements and dividing by the determinant H−B=σ. The results are as follows.

$$A = \frac{1}{\sigma}(B\Omega + HU) \text{ and } \tau = \frac{\sigma}{\Omega + U}$$

We demonstrate on the example shown in FIG. 8 and associated text where we know σ=0.75 and we had

|  | Cylinder of tIOL in D | Residual in D |
|---|---|---|
| Undercorrection | B = 3.75 | U = 0.26 |
| Overcorrection | H = 4.50 | Ω = 0.24 | and $$\tau = \frac{0.26 + 0.24}{0.75} = 1.50$$

A is obtained by cross multiplying as per equation above to get.

$$A = \frac{3.75 \times 0.24 + 4.50 \times 0.26}{0.75} = 2.76 \text{ D}.$$

Note that when given more than two options for correction along with the corresponding residuals it is possible to determine A and τ either by selecting a pair of equations as above or, if the equations are not linearly dependent, by solving the overdetermined system of equations, for example with a Moore Penrose pseudo inverse.

Terms $$\alpha = \frac{\sigma}{\tau}$$

"step" increment in diopter between two successive tIOLs, at the corneal plane $$\gamma = \frac{2\sin^2\lambda}{1 - 2\sin^2\lambda}$$

is also the fractional excess of A with respect to the midpoint m (See above)

λ angle of misalignment from all causes between the tIOL and the astigmatism to be corrected σ "step" increment in diopter between two successive tIOLs, at the IOL plane τ toricity ratio, conversion factor from cylinder at IOL plane to cylinder at corneal plane
χ crossing angle of overcorrection and undercorrection residuals as a function of λ
ω overcorrection relative to A
Ω overcorrection in diopters, at the corneal plane
A astigmatism to be corrected, at the corneal plane
b cylinder of undercorrecting tIOL at the corneal plane
B cylinder of undercorrecting tIOL at the IOL plane
C=cos 2λ
h cylinder of overcorrecting tIOL at the corneal plane
H cylinder of overcorrecting tIOL at the IOL plane
L cylinder of generic tIOL at cornea plane (See FIG. 1)

m midpoint between h and b, mean or midpoint of h and b
n (possibly integer) value determining pair of under and overcorrecting tIOL if integer $$n = \left\lceil \frac{\tau A}{\sigma} \right\rceil$$

R Generic residual astigmatism (See FIG. 1)
u undercorrection relative to A
U Undercorrection in diopters, at the corneal plane
"First Quantization"

$$H - B = \sigma$$

"Second Quantization"

$$H = n\sigma, n \text{ integer}$$

Overcorrection Limit $$\Omega_{max} = \frac{\sigma}{2\tau}[1 - \gamma(2n-1)]$$

Example of a Method
1) Determine σ by selection of manufacturer's sequence of tIOLs.
2) Determine τ by measuring the eye's axial length and K values using an appropriate formula or nomogram
3) For astigmatism A, calculate $$n = \left\lceil \frac{\tau A}{\sigma} \right\rceil$$

4) Select corresponding undercorrecting (n−1)σ and overcorrecting nσ candidate tIOLs.
5) Estimate χ based on surgical experience or on all contributions to misalignment, then calculate $$\gamma = \frac{2\sin^2\chi}{1 - 2\sin^2\chi}$$

or the approximation $$\gamma \approx \left(\frac{\chi_{deg}}{40}\right)^2$$

6) Substitute the values obtained in 1) to 5) in $$\Omega_{max} = \frac{\sigma}{2\tau}[1 - \gamma(2n-1)]$$

7) Overcorrect A with H if and only if $$\frac{H}{\tau} - A < \Omega_{max},$$

otherwise choose B=H−σ

Systems and Apparatuses

Figure 11:
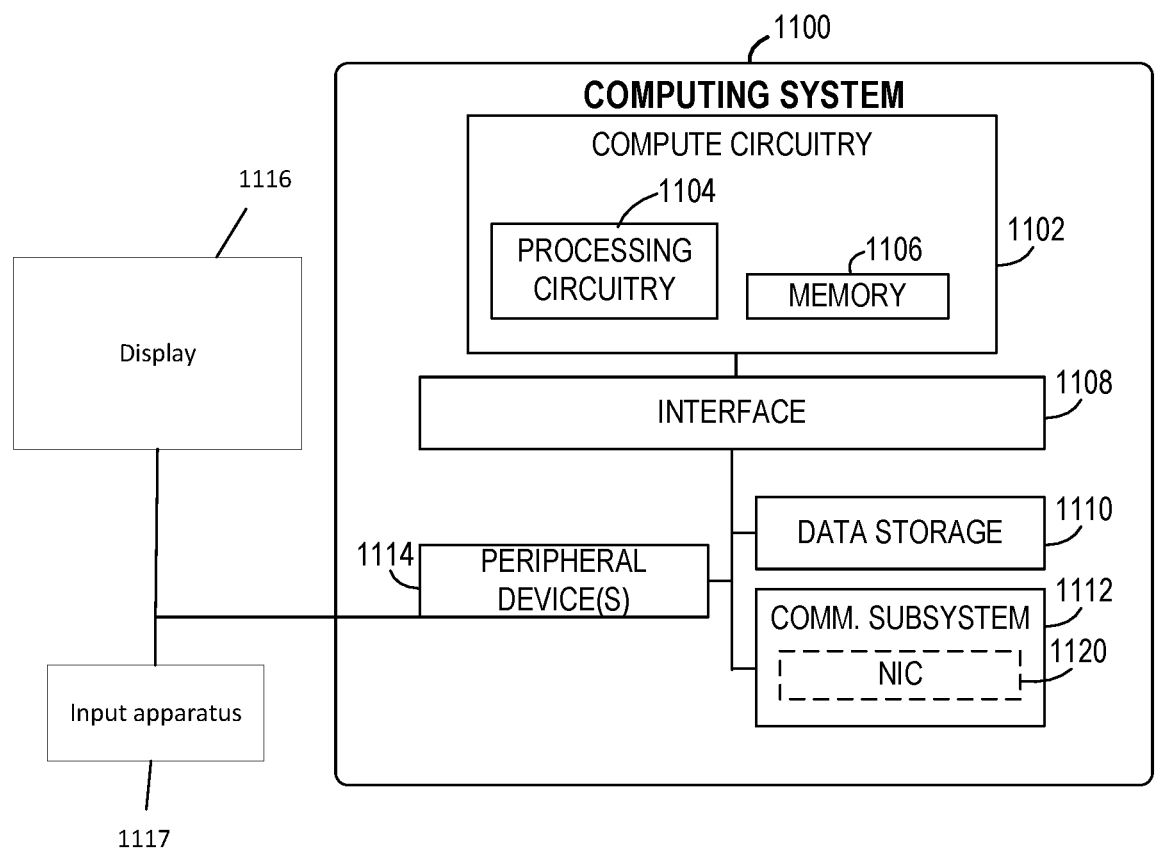
FIG. 11 is a block diagram of computer for implementing methods in accordance with embodiments.

In further examples, any of the methods described herein can be fulfilled using components depicted in FIG. 11. The computing system 1100 may be embodied as a type of device, appliance, computer, or other apparatus capable of communicating with other computing or networking components. For example, the computing system 1100 may be embodied as a personal computer, server, smartphone, a mobile compute device, a self-contained device having an outer case, shell, etc., or other device or system capable of performing the described functions.

The computing system 1100 includes a compute engine (also referred to herein as "compute circuitry") 1102, an input/output (I/O) subsystem 1108, data storage 1110, a communication circuitry subsystem 1112, and, optionally, one or more peripheral devices 1114. In other examples, respective compute devices may include other or additional components, such as those typically found in a computer (e.g., a display, peripheral devices, etc.). Additionally, in some examples, one or more of the illustrative components may be incorporated in, or otherwise form a portion of, another component.

The computing system 1100 may be embodied as any type of engine, device, or collection of devices capable of performing various compute functions. In some examples, the computing system 1100 may be embodied as a single device such as an integrated circuit, an embedded system, a field-programmable gate array (FPGA), a system-on-a-chip (SOC), or other integrated system or device. In the illustrative example, the computing system 1100 includes or is embodied as processing circuitry 1104 and a memory 1106. The processing circuitry 1104 may be embodied as any type of processor capable of performing the functions described herein (e.g., executing an application). For example, the processing circuitry 1104 may be embodied as a multi-core processor(s), a microcontroller, or other processor or processing/controlling circuit. In some examples, the processing circuitry 1104 may be embodied as, include, or be coupled to an FPGA, an application specific integrated circuit (ASIC), reconfigurable hardware or hardware circuitry, or other specialized hardware to facilitate performance of the functions described herein.

The memory 1106 may be embodied as any type of volatile (e.g., dynamic random-access memory (DRAM), etc.) or non-volatile memory or data storage capable of performing the functions described herein. Volatile memory may be a storage medium that requires power to maintain the state of data stored by the medium. Non-limiting examples of volatile memory may include various types of random-access memory (RAM), such as DRAM or static random-access memory (SRAM). In some examples, all or a portion of the memory 1106 may be integrated into the processing circuitry 1104. The memory 1106 may store various software and data used during operation such as one or more applications, data operated on by the application(s), libraries, and drivers.

The compute circuitry 1102 is communicatively coupled to other components of the computing system 1100 via the interface 1108, which may be embodied as circuitry and/or components to facilitate input/output operations with the compute circuitry 1102 (e.g., with the processing circuitry 1104 and/or the main memory 1106) and other components of the compute circuitry 1102. For example, the interface 1108 may be embodied as, or otherwise include, memory controller hubs, input/output control hubs, integrated sensor hubs, firmware devices, communication links (e.g., point-to-point links, bus links, wires, cables, light guides, printed circuit board traces, etc.), and/or other components and subsystems to facilitate the input/output operations. In some examples, the interface 1108 may form a portion of a system-on-a-chip (SoC) and be incorporated, along with one or more of the processing circuitry 1104, the memory 1106, and other components of the compute circuitry 1102, into the compute circuitry 1102.

The one or more illustrative data storage devices 1110 may be embodied as any type of devices configured for short-term or long-term storage of data such as, for example, memory devices and circuits, memory cards, hard disk drives, solid-state drives, or other data storage devices. Individual data storage devices 1110 may include a system partition that stores data and firmware code for the data storage device 1110. Individual data storage devices 1110 may also include one or more operating system partitions that store data files and executables for operating systems depending on, for example, the type of computing system 1100.

The communication circuitry 1112 may be embodied as any communication circuit, device, or collection thereof, capable of enabling communications over a network between the compute circuitry 1102 and another compute device (e.g., networked device). The communication circuitry 1112 may be configured to use any one or more communication technology (e.g., wired or wireless communications) and associated protocols or low-power wide-area (LPWA) protocols, etc.) to effect such communication.

The illustrative communication circuitry 1112 includes a network interface controller (NIC) 1120. The NIC 1120 may be embodied as one or more add-in-boards, daughter cards, network interface cards, controller chips, chipsets, or other devices that may be used by the computing system 1100 to connect with another compute device Additionally, in some examples, a respective computing system 1100 may include one or more peripheral devices 1114. Such peripheral devices 1114 may include any type of peripheral device found in a compute device or server such as audio input devices, a display, other input/output devices, interface devices, and/or other peripheral devices, depending on the particular type of the computing system 1100.

For example, peripheral devices 1114 can include a display 1116 or other output device. The display 1116 may be included to show information, such as tIOL settings, depictions of a patient's eye or portion thereof, sensor readings and other information. In some examples, the peripheral devices include an input apparatus 1117 to allow a user to input at least one of estimate misalignment, eye information, and lens information. The display 1116 can include a graphical user interface to display selected tIOL information, and the processing circuitry 1104 can be operably coupled to the input apparatus 1117 and the display 1116 to display the selected tIOL information. The input apparatus 1117 can include a touch screen or keypad may be included to accept input. The display 1116 may include any number of forms of audio or visual display, including simple visual outputs such as binary status indicators (e.g., light-emitting diodes (LEDs)) and multi-character visual outputs, or more complex outputs such as display screens (e.g., liquid crystal display (LCD) screens), with the output of characters, graphics, multimedia objects, and the like being generated or produced from the operation of the computing system 700. A display or console hardware, in the context of the present system, may be used to provide output and receive input of a computing system; to manage components or services of a computing system; identify a state of a computing component or service; or to conduct any other number of management or administration functions or service use cases.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method for selecting a toric intraocular lens (tIOL), the method comprising:
   receiving lens information for an overcorrecting tIOL and an undercorrecting tIOL for an eye to be treated with the selected tIOL;
   receiving an estimated misalignment; and
   selecting only one of the overcorrecting tIOL or the undercorrecting tIOL based on the lens information for the overcorrecting tIOL and the undercorrecting tIOL, and the estimated misalignment.

2. The method of claim 1, wherein the selecting further comprises:
   determining a minimum astigmatism; and
   selecting one of the overcorrecting tIOL and the undercorrecting tIOL based on the minimum astigmatism and astigmatism to be corrected.

3. The method of claim 2, wherein the selecting further comprises generating astigmatism to be corrected based on measured eye information.

4. The method of claim 2, wherein the selecting further comprises generating astigmatism to be corrected based on the lens information.

5. The method of claim 2, wherein the minimum astigmatism is determined based on at least the estimated misalignment and on the lens information.

6. The method of claim 2, wherein selecting one of the overcorrecting tIOL and the undercorrecting tIOL comprises selecting the overcorrecting tIOL if the minimum astigmatism is less than the astigmatism to be corrected.

7. The method of claim 1, wherein the selecting further comprises:
determining a maximum astigmatism; and
selecting one of the overcorrecting tIOL and the undercorrecting tIOL based on the maximum astigmatism and astigmatism to be corrected.

8. The method of claim 7, wherein the maximum astigmatism is based on at least the estimated misalignment and the lens information.

9. The method of claim 1, wherein the lens information includes an overcorrection value that indicates an amount of overcorrecting that would occur with the overcorrecting tIOL.

10. The method of claim 9, wherein the selecting one of the overcorrecting tIOL and the undercorrecting tIOL comprises selecting the overcorrecting tIOL if the overcorrection value is less than a maximum astigmatism to be overcorrected.

11. The method of claim 1, further comprising:
receiving user input comprising at least one of estimated misalignment, eye information, and lens information.

12. The method of claim 1, further comprising:
displaying, on a user display, the selected tIOL.

13. A system for selecting a toric intraocular lens (tIOL), the system comprising:
processing circuitry configured to:
receive lens information for an overcorrecting tIOL and an undercorrecting tIOL for an eye to be treated with the selected tIOL;
receive an estimated misalignment; and
select only one of the overcorrecting tIOL or the undercorrecting tIOL based on the lens information for the overcorrecting tIOL and the undercorrecting tIOL, and the estimated misalignment.

14. The system of claim 13, wherein the processing circuitry is further configured to determine a minimum astigmatism; and
select one of the overcorrecting tIOL and the undercorrecting tIOL based on the minimum astigmatism and astigmatism to be corrected.

15. The system of claim 14, wherein the selecting further comprises generating astigmatism to be corrected based on measured eye information.

16. The system of claim 14, wherein the selecting further comprises generating astigmatism to be corrected based on the lens information.

17. The system of claim 14, wherein the minimum astigmatism is determined based on at least the estimated misalignment and on the lens information.

18. The system of claim 13, wherein the processing circuitry is further configured to select one of the overcorrecting tIOL and the undercorrecting tIOL by selecting the overcorrecting tIOL if a minimum astigmatism is less than the astigmatism to be corrected.

19. The system of claim 13, wherein the processing circuitry is further configured to:
determine a maximum astigmatism; and
select one of the overcorrecting tIOL and the undercorrecting tIOL based on the maximum astigmatism and astigmatism to be corrected.

20. The system of claim 19, wherein the maximum astigmatism is based on at least the estimated misalignment and the lens information.

21. The system of claim 13, wherein the lens information includes an overcorrection value that indicates an amount of overcorrecting that would occur with the overcorrecting tIOL.

22. The system of claim 21, wherein the processing circuitry is further configured to select one of the overcorrecting tIOL and the undercorrecting tIOL by selecting the overcorrecting tIOL if the overcorrection value is less than a maximum astigmatism to be overcorrected.

23. The system of claim 13, wherein the system further comprises:
input apparatus to allow a user to input at least one of estimated misalignment, eye information, and lens information; and
a display comprising a graphical user interface to display the selected tIOL information,
wherein the processing circuitry is operably coupled to the input apparatus and the display and further configured to display the selected tIOL.

* * * * *